United States Patent [19]

Shaw

[11] Patent Number: 5,650,146

[45] Date of Patent: Jul. 22, 1997

US005650146A

[54] SILICONE BASED SKIN CARE PRODUCTS

[75] Inventor: Phillip David Shaw, Ashford, Great Britain

[73] Assignee: Quest International B.V., Naarden, Netherlands

[21] Appl. No.: 532,597

[22] PCT Filed: Mar. 4, 1994

[86] PCT No.: PCT/EP94/00638

§ 371 Date: Oct. 5, 1995

§ 102(e) Date: Oct. 5, 1995

[87] PCT Pub. No.: WO94/22420

PCT Pub. Date: Oct. 13, 1994

[30] Foreign Application Priority Data

Apr. 5, 1993 [EP] European Pat. Off. ............ 93200984

[51] Int. Cl.⁶ .................................................. A61K 31/765
[52] U.S. Cl. .......................... 424/78.03; 424/43; 424/59; 424/78.02; 424/400; 424/401; 424/407; 514/63; 514/937; 514/938; 514/944; 514/957

[58] Field of Search ..................... 514/944, 937, 514/938, 957, 63; 424/78.02, 78.03, 59, 400, 401, 407, 43

[56] References Cited

U.S. PATENT DOCUMENTS

| | | | |
|---|---|---|---|
| 4,900,542 | 2/1990 | Parrotta et al. | 424/66 |
| 5,162,378 | 11/1992 | Guthauser | 514/785 |
| 5,176,898 | 1/1993 | Goldberg et al. | 424/47 |

FOREIGN PATENT DOCUMENTS

| | | |
|---|---|---|
| 25 31 260 | 1/1977 | Germany. |
| 2 206 048 | 12/1988 | United Kingdom. |

*Primary Examiner*—Terressa Mosley
*Attorney, Agent, or Firm*—Cushman Darby & Cushman IP Group Pillsbury Madison & Sutro LLP

[57] ABSTRACT

The invention is concerned with silicone-based skin care products which are applied to the skin as aerosols and form a clear gel on the skin. The skin care products comprise 20–70% w/w of a silicone based water-in-oil microemulsion and 30–80% w/w of a volatile diluent. Preferably the microemulsion has a viscosity of between 1000 and 10,000 mPas.

9 Claims, No Drawings

SILICONE BASED SKIN CARE PRODUCTS

This application is a 371 of PCT/EP94/00638, Mar. 4, 1994.

The invention is concerned with silicone based skin care products. More particularly the invention is concerned with such products which are applied to the skin as aerosols and form a clear gel on the skin.

BACKGROUND OF THE INVENTION

Gels which are applied to the skin as aerosols are known in the art. In such products the volatile propellant acts as a diluent for the viscous gel in the aerosol container. When applied to the skin, the propellant evaporates and leaves the product as a gel or foam. Such products are exemplified e.g in: JP-A-4.103526 which describes foamy gels for pain relief and cooling of the skin, containing (polyoxyethylene) sorbitan fatty acid esters as the gellifying agent; EP-A-0 134 964 describing liquid products which contain polyoxypropylene-polyoxyethylene copolymers as the gelling agent and a medicament and which are applied as a foam and transform into a gel on contact with the skin; EP-A-0 423 695 describing a similar product which contains polyoxyetylene surfactant and is applied as a foam; EP-A-0 207 022 describing a product which is applied from aerosol containers and contains solid particles of water absorbent material such as starch or polyacrylamide and in addition some gel-forming polymer; U.S. Pat. Nos. 4,495,168 and 4,495,169 both describing liquid products which contain polyoxyethylene-polyoxypropylene or polyoxyethylene-polyoxybutylene block copolymers as the gelling agent and which form a gel on contact with the skin and are useful for various applications such as shaving cream. However, none of these products appear to form a clear gel on the skin.

Clear gels, on the other hand, are much appreciated as skin care products for various purposes because of their attractive appearance, and can be made from various starting materials. Silicone based clear gels are are well known among such products. Examples have been described in U.S. Pat. Nos. 4,673,570, 4,900,542, WO 92/05767 and GB-A-2 079 300. The advantages of silicone based microemulsion gels have been described in the brochure "Silicone Emulsifiers" of A. Zombeck, Dow Corning Europe S. A. However, none of these products have been described as being suitable for application to the skin as an aerosol, while still producing the desired clear gel after application.

SUMMARY OF INVENTION

It has now been found that certain silicone based skin care products, comprising a silicone based water-in-oil microemulsion diluted with a volatile diluent, can be applied to the skin as an aerosol and still produce a non-running clear gel on the skin. Thus, the invention provides silicone based skin care products for application as an aerosol and forming a clear gel on the skin, which comprise 20–70% w/w of a silicone based water-in-oil microemulsion and 30–80% w/w of a volatile diluent.

For the purposes of this invention an "aerosol" is defined as a multitude of very fine droplets of liquid as is normally produced from standard pressurized aerosol containers or pump-spray containers, such as are currently in use for many cosmetic and skin care products. When such aerosol, wherein the droplets of liquid consist of silicone based skin care product according to the invention, comes in contact with the skin, the volatile diluent evaporates and the aerosol leaves a clear, non-running gel on the skin Also, for the purposes of this invention a "silicone based water-in-oil microemulsion is a microemulsion wherein the emulsifier is mainly or exclusively a silicone emulsifying agent and the oil phase contains an appreciable quantity of polyorganosiloxane-type liquid. Accordingly, a silicone based skin care product as referred to herein is a skin care product comprising such "silicone based water-in-oil microemulsion".

Thus, the invention also provides a method for applying a silicone based clear gel to the skin, the method comprising the steps of filling a silicone based skin care product, comprising 20–70% w/w of a silicone based water-in-oil microemulsion and 30–80% w/w of a volatile diluent, into a pressurized or pump-spray aerosol container and spraying it on the skin.

DETAILED DESCRIPTION OF THE INVENTION

The silicone based water-in-oil microemulsion typically comprises (in % w/w of the microemulsion):

| | |
|---|---|
| 0.5–3.5% | Silicone emulsifying agent, |
| 9–47% | Polyorganosiloxane liquid, |
| 20–60% | Water, |
| 20–40% | Propylene glycol, |
| 5–60% | Glycerine, |
| 0–20% | Active skin care material |

Particularly suitable emulsifying agents are polyether substituted silicones of the Dimethycone Copolyol type. They are commercially available as a 10% solution in a polyorganosiloxane liquid (Cyclomethicone). Thus, particularly suitable microemulsions have the following composition:

| | |
|---|---|
| 5–35% | 10% Dimethicone Copolyol in Cyclomethicone, |
| 5–15 | Cyclomethicone, |
| 20–60% | Water, |
| 20–40% | Propylene glycol, |
| 5–60% | Glycerine, |
| 0–20% | Active skin care material |

The silicone based skin care products according to the invention already have a moisturizing effect on the skin as well as producing a pleasant silky feeling even without any additional active skin care materials being present in the product. However, they also are excellent carriers for other active skin care materials. Active skin care materials are materials which have a desired functional effect on the skin after application thereto, such as fragrances, perspiration counteracting materials (e.g. aluminium or zinc salts), bactericides or bacteriostats, moisturizers, vitamins, cooling agents, suncreen agents, etc. Thus, by selecting the right (combination of) active skin care materials, the silicone based skin care products can e.g. be made to perform one or more of the following functions: moisturiser; body spray; deodorant; antiperspirant; cooling gel; sunscreen; after-sun care; pre-shaving, shaving or after-shaving product.

The silicone based water-in-oil microemulsion, forming part of the skin care product, is a transparent or translucent, rather viscous microemulsion. Too low a viscosity will make the gel run or drip after application to the skin. Too high a viscosity, on the other hand, may entrap the volatile diluent and prevent it from evaporating after application to the skin and may thus make the gel appear opaque. Also, too high a viscosity may make the microemulsion fail to adequately mix with the diluent. Preferably, the microemulsion will have a viscosity of between 1,000 and 10,000 mPas.

The volatile diluent preferably comprises 30–80% w/w (of the total skin care product) of a volatile hydrocarbon and optionally 0–40% w/w of a volatile polyorganosiloxane as a supplemental diluent. The term "volatile" is meant to denote a liquid sufficiently volatile to quickly evaporate after the aerosol has come into contact with the skin. Diluents (or diluent mixtures) with too low a volatility may again cause the gel to run or drip before the diluent has sufficiently evaporated. Very suitable hydrocarbons are propane, n-butane, iso-butane and iso-pentane or mixtures thereof. A suitable volatile polyorganosiloxane may be found among cyclomethicone/dimethycone mixtures.

The skin care product is suitably prepared by mixing the components for the silicone based microemulsion, whereafter this microemulsion is mixed with the volatile diluent. The total product may then not be transparant or translucent any more, but yet produces a clear gel after application to the skin.

The invention is further illustrated by the following example but not in any way limited thereto.

EXAMPLE

A clear gel deodorant was prepared using the ingredients and following the procedure described below:

|   |   | % w/w |
|---|---|---|
| A | DC 3225C[1] | 10.00 |
|   | DC 244[2] | 7.00 |
| B | Propylene glycol | 31.00 |
|   | Triclosan | 0.10 |
|   | Glycerine | 15.00 |
|   | Perfume | .50 |
|   | Deionised water | to make up to 100 |

[1] A 10% dispersion of Dimethicone Copolyol in Cyclomethicone marketed by Dow Corning Int. Ltd, Brussels, Belgium
[2] Cyclomethicone/dimethicone marketed by Dow Corning Int. Ltd The components A were mixed together. The Triclosan was dissolved in the propylene glycol whereafter the remaining components B were added. Mixture A was vigorously stirred while mixture B was slowly added and thus a thick pourable microemulsion was obtained.

This microemulsion was filled into suitable lacquered tin-plate or aluminium aerosol cans which were closed and thereafter charged with propellant in a ratio of 65% w/w of microemulsion to 35% w/w of propellant. The propellant consisted of a mixture of deodorized n-butane, isobutane and/or propane, having a vapour pressure of 377 kPa.

I claim:

1. Silicone based skin care produces for application as an aerosol and forming a clear gel on the skin, which comprise 20–70% w/w of a silicone based water-in-oil microemulsion and 30–80% w/w of a volatile diluent.

2. Silicone based skin care products according to claim 1, wherein the silicone based water-in-oil microemulsion comprises (in % w/w of the microemulsion):

| 0.5–3.5% | Silicone emulsifying agent, |
|---|---|
| 9–47% | Polyorganosiloxane liquid, |
| 20–60% | Water, |
| 20–40% | Propylene glycol, |
| 5–60% | Glycerine, |
| 0–20% | Active skin care material |

3. Silicone based skin care products according to claim 2, wherein the silicone based water-in-oil microemulsion comprises:

| 5–35% | 10% Dimethicone Copolyol in Cyclomethicone, |
|---|---|
| 5–15% | Cyclomethicone, |
| 20–60% | Water, |
| 20–40% | Propylene glycol, |
| 5–60% | Glycerine, |
| 0–20% | Active skin care material |

4. Silicone based skin care products according to any one of claims 1–3, wherein the silicone based water-in-oil microemulsion has a viscosity of between 1,000 and 10,000 mPas.

5. Silicone based skin care products according to claim 2, wherein the volatile diluent comprises of 30–80% w/w of a volatile hydrocarbon and optionally 0–40% w/w of a volatile polyorganosiloxane as a supplemental diluent.

6. Silicone based skin care products according to claim 5, wherein the volatile hydrocarbon diluent consists of one or more of: propane, n-butane, iso-butane and iso-pentane.

7. Silicone based skin care products according to claim 5, wherein the volatile polyorganosiloxane is a cyclomethicone/dimethicone mixture.

8. Silicone based skin care products according to claim 2, wherein the active skin care materials are chosen such as to make the product perform on the skin one or more of the functions of: fragrance; moisturiser; body spray; deodorant; antiperspirant; cooling gel; sunscreen; after-sun care; pre-shaving, shaving, after-shaving product.

9. Method for applying a silicone biased clear gel to the skin comprising the steps of filling a silicone based skin care product according to claim 2 into a pressurized or pump-spray aerosol container and spraying it on the skin.

* * * * *